United States Patent
Khajavi et al.

(10) Patent No.: US 9,149,305 B2
(45) Date of Patent: Oct. 6, 2015

(54) SPINOUS PROCESS FIXATION PLATE AND MINIMALLY INVASIVE METHOD FOR PLACEMENT

(75) Inventors: Kaveh Khajavi, Lawrenceville, GA (US); David E. Lane, Lawrenceville, GA (US)

(73) Assignee: Latitude Holdings, LLC, Atlanta, GA (US)

( * ) Notice: Subject to any disclaimer, the term of this patent is extended or adjusted under 35 U.S.C. 154(b) by 443 days.

(21) Appl. No.: 12/904,725

(22) Filed: Oct. 14, 2010

(65) Prior Publication Data
US 2011/0087285 A1 Apr. 14, 2011

Related U.S. Application Data

(60) Provisional application No. 61/251,514, filed on Oct. 14, 2009.

(51) Int. Cl.
*A61B 17/70* (2006.01)

(52) U.S. Cl.
CPC ......... *A61B 17/7065* (2013.01); *A61B 17/7068* (2013.01)

(58) Field of Classification Search
CPC ................ A61B 17/7065; A61B 17/7068
USPC ............. 606/248, 249, 105, 90; 623/17.11, 623/17.15, 17.16
See application file for complete search history.

(56) References Cited

U.S. PATENT DOCUMENTS

| | | | |
|---|---|---|---|
| 6,039,761 A | 3/2000 | Li et al. | |
| 6,626,944 B1 | 9/2003 | Taylor | |
| 6,946,000 B2 | 9/2005 | Senegas et al. | |
| 7,377,942 B2 | 5/2008 | Berry | |
| 8,048,120 B1 * | 11/2011 | Fallin et al. | 606/249 |
| 8,308,769 B2 * | 11/2012 | Farr | 606/249 |
| 2003/0040746 A1 * | 2/2003 | Mitchell et al. | 606/61 |
| 2005/0143737 A1 * | 6/2005 | Pafford et al. | 606/61 |
| 2005/0203624 A1 | 9/2005 | Serhan et al. | |
| 2005/0261768 A1 | 11/2005 | Trieu | |
| 2006/0271194 A1 * | 11/2006 | Zucherman et al. | 623/17.11 |
| 2007/0270840 A1 * | 11/2007 | Chin et al. | 606/61 |
| 2008/0027438 A1 * | 1/2008 | Abdou | 606/61 |
| 2008/0046007 A1 | 2/2008 | Schwemberger et al. | |
| 2008/0046085 A1 | 2/2008 | Zucherman et al. | |
| 2008/0058937 A1 | 3/2008 | Malandain et al. | |
| 2008/0071380 A1 | 3/2008 | Sweeney | |
| 2008/0108990 A1 | 5/2008 | Mitchell et al. | |
| 2008/0109082 A1 | 5/2008 | Fink et al. | |
| 2008/0183211 A1 | 7/2008 | Lamborne et al. | |
| 2008/0294263 A1 * | 11/2008 | Altarac et al. | 623/17.16 |
| 2008/0300635 A1 * | 12/2008 | Lieponis | 606/280 |

(Continued)

FOREIGN PATENT DOCUMENTS

| WO | WO2007111979 | 10/2007 |
|---|---|---|
| WO | WO2009098536 | 8/2009 |

*Primary Examiner* — Jan Christopher Merene
*Assistant Examiner* — Atiya Mahmud
(74) *Attorney, Agent, or Firm* — McHale & Slavin, P.A.

(57) ABSTRACT

The invention is directed to a laterally inserted spinous process plating device and a method for installing the device using a minimally invasive procedure. The device includes a partially threaded bolt as well as a contralateral and ipsilateral fixation plates, a deployment nut, a lag nut and a locking nut. Each fixation plate includes a pair of wing portions that are pivotally connected to one another to facilitate installation. The each of the fixation plates includes anchoring elements.

10 Claims, 10 Drawing Sheets

(56) References Cited

U.S. PATENT DOCUMENTS

2010/0174373 A1* 7/2010 Galley et al. ............... 623/17.13
2010/0217272 A1* 8/2010 Baughman et al. ............. 606/99
2010/0241166 A1* 9/2010 Dwyer et al. ................. 606/249
2011/0046674 A1* 2/2011 Calvosa et al. ............... 606/249

* cited by examiner

SPINOUS PROCESS FIXATION PLATE AND MINIMALLY INVASIVE METHOD FOR PLACEMENT

CROSS REFERENCE TO RELATED APPLICATIONS

This application claims the benefit of provisional application 61/251,514, entitled Spinous Process Fixation Plate and Minimally Invasive Method for Placement, filed on Oct. 14, 2009, the entire contents of which is hereby expressly incorporate by reference.

FIELD OF THE INVENTION

The present invention is directed to a spinous process fixation plate and a method of percutaneous lateral placement.

BACKGROUND OF THE INVENTION

The human spine is arranged as a series of vertebrae separated by intervertebral discs often referred to as the backbone. These intervertebral discs perform a variety of functions. In particular the discs allow the spine to twist and flex as well as functioning as a cushion to absorb force or shock between adjacent vertebrae. Spinal discs are subject to physical degeneration either as a result of physical injury, age, disease, genetic propensity or a combination thereof. The degenerative disc may lessen the discs ability to allow relative movement between adjacent vertebrae and reduce its cushioning characteristics and as the disc breaks down the spacing between adjacent vertebras will be reduced. The rupturing, tearing of the disc may also lead to a condition known as spinal stenosis. Spinal stenosis is a progressive narrowing if the opening of the spinal canal. Each vertebra has a hole or channel passing through it. These holes are in alignment and form the spinal canal. A relatively large bundle of nerves known as the spinal cord runs through the spinal canal. When the spinal cord narrows the nerve roots in the spinal cord are compressed. The pressure on the nerve roots may cause chronic pain and numbness and in some instances cause loss of motive functions within the body. Most often the lower back and legs are affected by spinal stenosis. Cervical spinal stenosis is a narrowing if the vertebrae of the neck referred to as cervical vertebrae. In addition to exerting pressure on the spinal cord cervical stenosis can also put pressure on the arteries entering the spinal column thereby limiting the flow of blood to the other portions of the spinal cord.

Spinal stenosis and disc degeneration can be progressive diseases. Quite often these diseases are treated surgically by reestablishing a more normal spacing between the adjacent vertebrae. The restoration of the vertebral spacing may provide the necessary to relieve the pressure on the affected nerve tissue. The surgical procedure is intended to remove bone and other tissues that have entered the spinal canal or put pressure on the spinal cord. Often it is necessary to surgically remove the disc material as well. In general the restoration of the vertebral spacing is achieved by insertion of a spacer. The spacer element is formed from bone, metal or plastic material and enables the vertebrae to grow together, or fuse. Typically bone plates and or pedicle screws are utilized to stabilize and maintain proper alignment between adjacent vertebrae as they are fused together.

The installation of these intervertebral spacers significantly within the patient's body and proximate to the spine can be an invasive process requiring prolonged hospitalization and extended amounts of rehabilitation. It has been well recognized that a spacer device that can be deployed in a minimally invasive manner would result in a substantial improvement in the outcome of the procedure.

DESCRIPTION OF THE PRIOR ART

A number of prior art patents disclose various spinous process plates for the fixation of adjacent vertebrae.

U.S. Pat. No. 6,039,761, to Li et al, discloses an intervertebral spacer comprises a multiplicity of interconnected wall elements collapsible to a first configuration wherein the wall elements are disposed in a compact arrangement, and expandable to a second configuration wherein the wall elements are disposed in an expanded arrangement which is open at a generally planar top and a generally planar bottom thereof.

U.S. Pat. No. 6,626,944, to Taylor, discloses a prosthesis that is made of a material which is multi-directionally flexible and elastic, and comprises an interspinous portion having a thickness slightly greater than the anatomical interspinous space when the spine is in lordosis. The prosthesis has two pairs of lugs projecting longitudinally on either side of its interspinous portion, these lugs having substantial heights in relation to the total height of the prosthesis, namely, for each pair of lugs, of the order of 30 to 45% of this total height; each pair of lugs is integral with the said interspinous portion and delimits a deep recess which is able to receive the corresponding spinous apophysis without play, with a wide surface area of contact between these lugs and this apophysis.

U.S. Pat. No. 6,946,000, to Senegas et al, discloses an intervertebral implant including a wedge which is inserted between two spinous processes and has two opposite grooves in which the spinous processes engage. The grooves have substantially parallel axes, and each of the grooves is defined by two flanges. The wedge has at least one central opening between the two grooves and the central opening passes completely through the wedge along an axis Ac that is substantially parallel to the axes Ag1 and Ag2 of said grooves. The wedge is elastically deformable.

U.S. Pat. No. 7,377,942, to Berry, discloses a prosthetic device for interposition in a space left by one or more excised vertebral posterior structures. The prosthetic device comprises a lamina bridge having an inferior portion for replacing an excised lamina; at least one inferior facet replacement device, connected to the inferior portion of the lamina bridge, to replace an excised inferior articular process; and at least one superior facet replacement device to replace an excised superior articular process. The at least one superior facet replacement device articulates with the at least one inferior facet replacement device.

U.S. Publication No. 2005/0203624, to Serhan et al, discloses an interspinous process having a general horseshoe shape, a cushion element within the horseshoe and a porous coating on its outer surface.

U.S. Publication No. 2005/0261768, to Trieu, discloses a method of providing an interspinous spacer between adjacent spinous processes includes: providing a spacer that is configurable to a collapsed configuration and to an expanded configuration, where the collapsed configuration presents an implantation profile that is at least 10% smaller than the corresponding profile when the spacer is in its expanded configuration; then causing the spacer to assume its collapsed configuration; then introducing the spacer into a medical patient while the spacer is in its collapsed configuration; and then allowing the spacer to assume its expanded configuration while positioned between adjacent spinous processes in a medical patient.

U.S. Publication No. 2008/0046087, to Zucherman et al, discloses an implant comprising a spacer for defining a minimum space between adjacent spinous processes, a distraction guide for piercing and distracting an interspinous ligament during implantation, and a binder for limiting or preventing flexion motion of the targeted motion segment. The binder can be secured to a brace associated with the implant during implantation by a capture device. In one embodiment, the capture device includes a fixed piece extending from the brace and a slidable piece associated with the fixed piece. A fastener can be rotated to pinch the binder between the slidable piece and a wall of the brace, securing the binder. A physician need not know the length of the binder prior to implantation, reducing the time required to perform a procedure.

U.S. Publication No. 2008/0058937, to Malandain, discloses an apparatus that includes a support member and a retention member. The support member has at least a portion configured to be disposed between a first spinous process and a second spinous process. The retention member is movably coupled to an end portion of the support member. The retention member is configured to displace a bodily tissue. The retention member is configured to move relative to the support member from a first position to a second position. The retention member is configured to limit movement of the support member along the longitudinal axis and relative to the first spinous process and the second spinous process when in the second position.

U.S. Publication No. 2008/0109082, to Fink et al, discloses an implant for restoring the height of and alleviating pressure on an intervertebral space of a human or animal spinal column, comprising at least two bearing elements for a spinous process each for abutting and/or securing the implant on one or two spinous processes of adjacent vertebra of the spinal column, such that as far as possible only one single operation is required to restore the height of and alleviate pressure on the intervertebral space. The implant is produced from a biocompatible, resorbable material.

U.S. Publication No. 2008/0183211, to Lamborne, discloses a spinous process implant and associated methods and instrumentation for inserting the implant. The implant limits the maximum spacing between the spinous processes and at least one transverse opening to facilitate tissue in-growth. The implant includes a spacer and separate extensions engageable with the spacer. The spacer is provided in a variety of lengths and superior to inferior surface spacing. The implant also includes a spacer and a cerclage element offset from the midline of the spacer in use so that the spacer defines a fulcrum and the cerclage element is operative to impart a moment to the vertebrae about the spacer.

SUMMARY OF THE INVENTION

The invention is directed to a laterally inserted spinous process plating device and a method for installing the implant using a minimally invasive procedure.

Lumbar arthrodesis is often utilized to treat a variety of degenerative spinal conditions. Posterior approaches have traditionally been used, with varying degrees of success. Posterior approaches can be associated with significant morbidity however. Prolonged muscle dissection and retraction can result in paraspinal muscle atrophy and fibrosis, which may result in prolonged pain and disability. As a result, an anterior or lateral approach, disectomy and interbody fusion has been advocated by many as an alternative to posterior arthrodesis. Generally, a more complete disectomy can be performed, which may provide a better surface area for fusion, as well as a larger cross-sectional area in which to sustain load and resist subsidence. Anterior lumbar arthrodesis may result in improved expansion of the disc space and increased local disc angle, which may improve spinal sagittal balance more effectively than posterior lumbar arthrodesis.

Oftentimes however, anterior or lateral interbody fusion requires supplemental instrumentation to increase stability. In the case of the lateral approach to lumber fusion, a lateral lumber plate can be used at the time of interbody fusion, but because only the lateral aspect of the anterior lumbar bodies are being fixated on one side, transitional forces may be turned into shear or rotation, and may be biomechanically suboptimal. For the same reason, unilaterally placed pedicle screw rod fixation in the lateral position suffers from the same constraints. Many surgeons feel that facet screws, or midline interspinous process fixation, is required to maximize stability and minimize the risk of construct failure. Currently the only way to achieve that goal is to place the patient in the prone position, and perform a second operation. This adds significant overall time to the surgery, and also requires one or more new incisions in the back to place the instrumentation, with its associated increased risk and morbidity. Ideally, if a method could be devised where midline posterior fixation can be obtained while the patient is already in the lateral position, then one could reduce the patient's operative time, risk and mobility, while at the same time increasing overall construct stability. A laterally placed minimally invasive intraspinous fixation device would ideally address that situation. Such an intraspinous device could be placed without any additional incisions and without the time necessary to place the patient in the prone position for a second operation. Moreover, because no posterior incision is required, there is a complete preservation of the posterior tension band, including the paraspinal muscles and the supraspinous ligament. Prior to this invention no such device exists in the field.

Accordingly, it is an objective of the instant invention to provide a spinous process plate that can be used to midline posterior fixation and fusion and laterally delivered percutaneously.

It is a further objective of the instant invention to provide a spinous process plate that can be positioned and installed without the removal of the supraspinous ligament, and the paraspinal muscles.

It is yet another objective of the instant invention to provide a spinous fixation device that will reduce the risk of morbidity, reduce the patients' operative time, and decrease the amount of time required for recuperation.

It is a still further objective of the invention to provide a method for laterally inserting a spinous process plate in a minimally invasive procedure.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
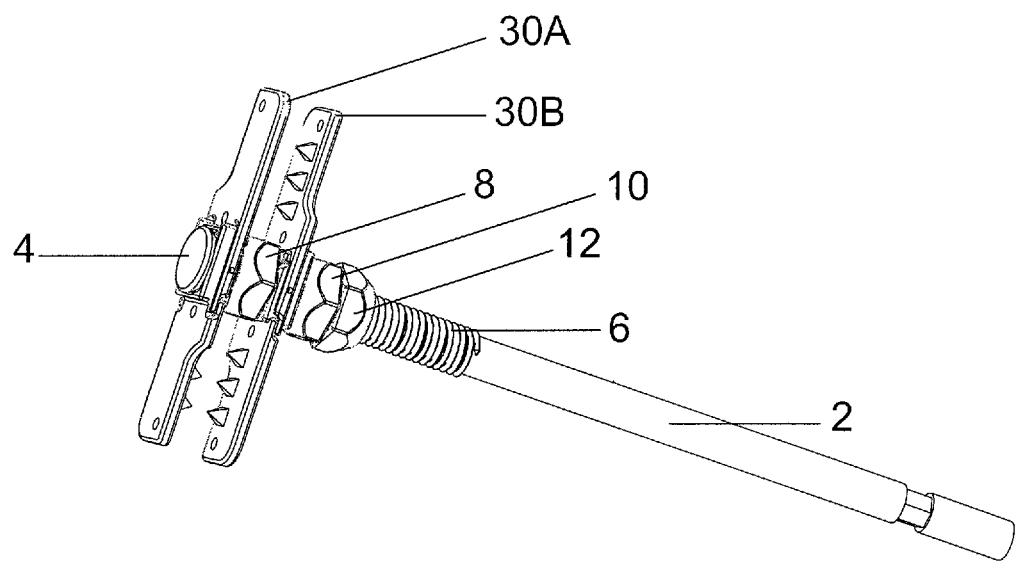
FIG. 1 is a perspective view of the spinous process plates in an assembled orientation with the vertebrae and disc removed for clarity.

FIG. 1 is a perspective view of the spinous process plates in an assembled orientation with the vertebrae and disc removed for clarity. As shown the spinous process bone fixation device includes a partially threaded bolt 2 having an enlarged bolt head 4 at one end and an engaging surface at the opposite end. The bolt 2 also includes a threaded portion 6 that extends from the head 4 partially along the length of the bolt 2. The device also includes a contralateral fixation plate 30A and an ipsilateral fixation plate 30B. Plates 30A and 30B are identical in construction. The device further includes a deployment nut 8, a lag nut 10 and a locking nut 12.

Figure 2:
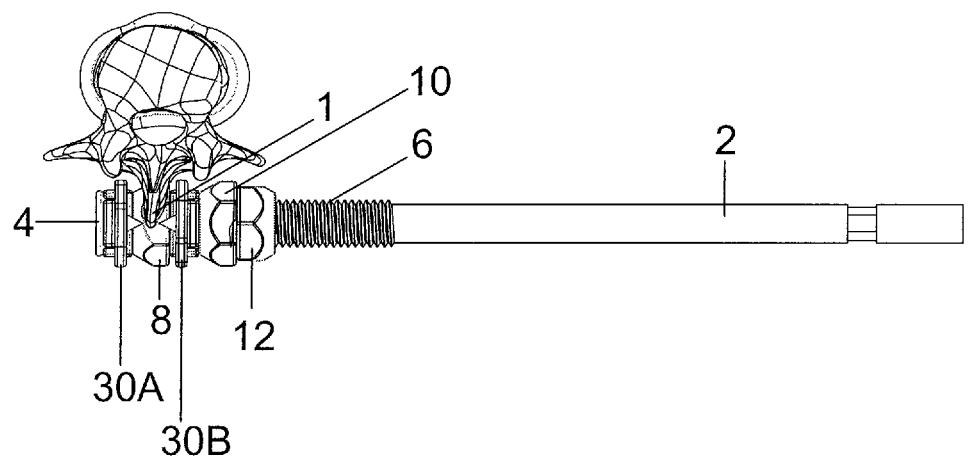
FIG. 2 is a top view of the spinous process fixation plate in operative engagement with the spinous process bone.

FIG. 2 is a top view of the spinous process fixation plate in operative engagement with the spinous process bone 1. The top surface of the contralateral fixation plate 30A engages the spinous process bone 1 and the ipsilateral fixation plate 30B engages the spinous process bone form the opposite side. Head 4 of bolt 2 and deployment screw 8 retain contralateral plate 30A in position and deployment nut 8 and lag nut 10 secure ipsilateral fixation plate 30B. In addition, a lock nut 12 serves to maintain the components in a fixed relationship.

Figure 3:
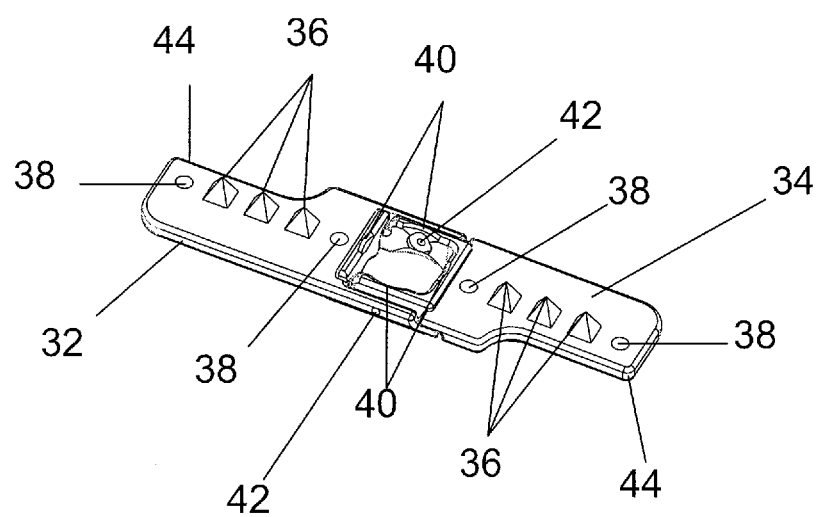
FIG. 3 is a top perspective view of one of the two spinous process fixation plates.
Figure 4:
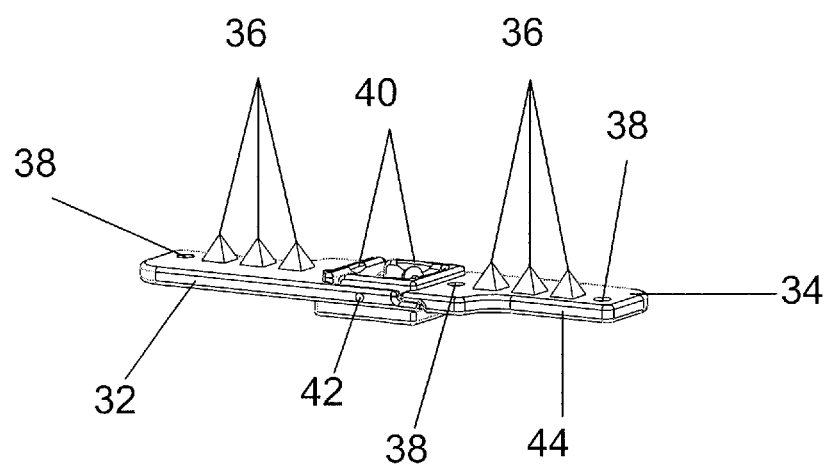
FIG. 4 is a side perspective view of one of the two spinous process fixation plates.

FIG. 3 is a top perspective view and FIG. 4 is a side perspective view of one of the two spinous process fixation plates, the contralateral 30 A and the ipsilateral 30B. Each fixation plate includes a first wing portion 32 and a second wing portion 34. The top surface of each which portion includes a series of teeth 36. In addition both the first wing portion 32 and the second wing portion 34 include a plurality of threaded apertures 38 to permit additional anchoring of the fixation plates to the spinous process bone 1 and or to one another. The top surfaces of wing portions 32 and 34 also include beveled surfaces 40 to facilitate the seating of deployment nut 8. Both the first and second wing portions each include a pair of apertures that when brought into alignment are configured to receive pivot elements 42 to allow the wings to pivot with respect to one another. Pivot elements 42 are formed as apertures and pins that are formed as threaded in pin members, molded parts, rivets, or the like. Each of the wing portions 32 and 34 include an offset portion 44 that allows for multiple levels of fixation to be addressed thereby negating the problem of plate overlap.

Figure 5A:
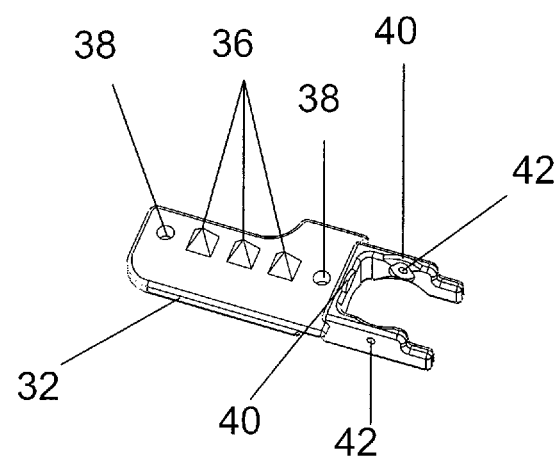
FIG. 5A is a top view of the first wing portion of one of the spinous process plates.
Figure 5B:
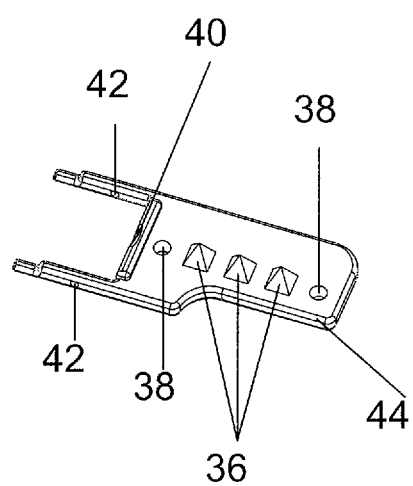
FIG. 5B is a top view of the second wing portion of one of the spinous process plates.

FIGS. 5A and 5B are top perspective views of the first wing portion 32 and second wing portion 34 of the spinous fixation plate (30A and 30B) that are shown separately for purposes of clarity. As shown, the top surfaces of first portion 32 and second portion 34 each include teeth 36. The threaded apertures 38 are available for optional use to fasten the fixation device into the spinous process bone and or from one plate to another. In the assembled position threaded apertures 38 on spinous fixation plates 30A and 30B are in alignment with one another and can be joined together through a hole formed in the spinous process bone. First wing portion 32 has three recesses 40 and second wing portion 34 has one recess that are configured to engaged and properly seat deployment nut 8. Each wing member has a generally U shaped end having a bottom wall connected to a pair of parallel side walls. The legs of the U shaped end are sized such side walls of the U shaped member on wing 34 telescope within the side walls of the U shaped member 32. Each U shaped end includes a pair of apertures, each formed on the side walls that are sized and configured to be brought into alignment for receipt of pivot elements 42. Each of the wing portions 32 and 34 include an offset portion 44 that allows for multiple levels of fixation to be addressed thereby negating the problem of plate overlap.

Figure 5C:
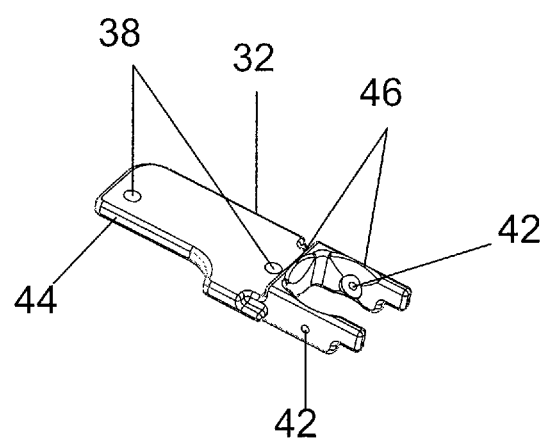
FIG. 5C is a bottom view of the first wing portion of one of the spinous process plates.
Figure 5D:
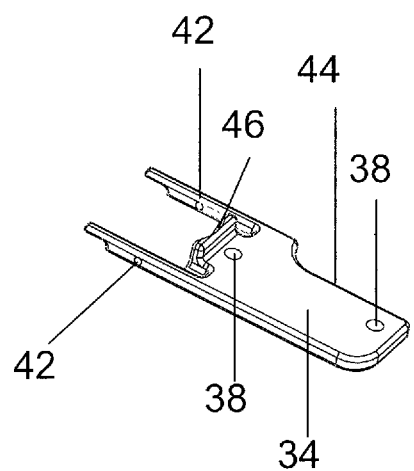
FIG. 5D is a bottom view of the second wing portion of one of the spinous process plates.

FIGS. 5C and 5D are bottom perspective views of the first wing portion 32 and second wing portion 34 of the spinous fixation plate (30A and 30B) that are shown separately for purposes of clarity. As shown, the bottom surfaces of first portion 32 and second portion 34 are smooth. First wing portion 32 has three recesses 46 and second wing portion 34 has one recess 46 that are configured to engaged and properly seat bolt head 4 to contralateral fixation plate 30A and lag nut 10 on ipsilateral fixation plate 30B. Also shown as apertures 38, pivot members 42, and offsets 44 which have been previously described.

Figure 6:
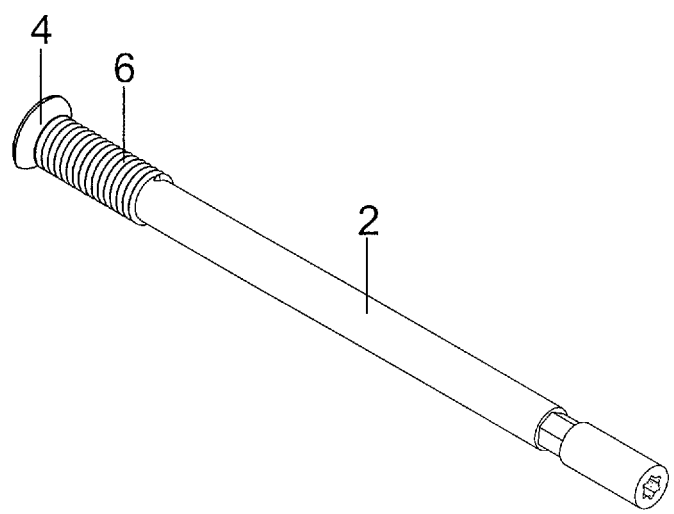
FIG. 6 is a perspective view of a partially threaded bolt used to deliver and retain the spinous process fixation plates in position.

FIG. 6 is a perspective view of a partially threaded bolt 2 used to deliver and retain the spinous process fixation plates in position. Bolt 2 includes a partially threaded portion 6 and a bolt head 4 formed on the end of the bolt.

Figure 7:
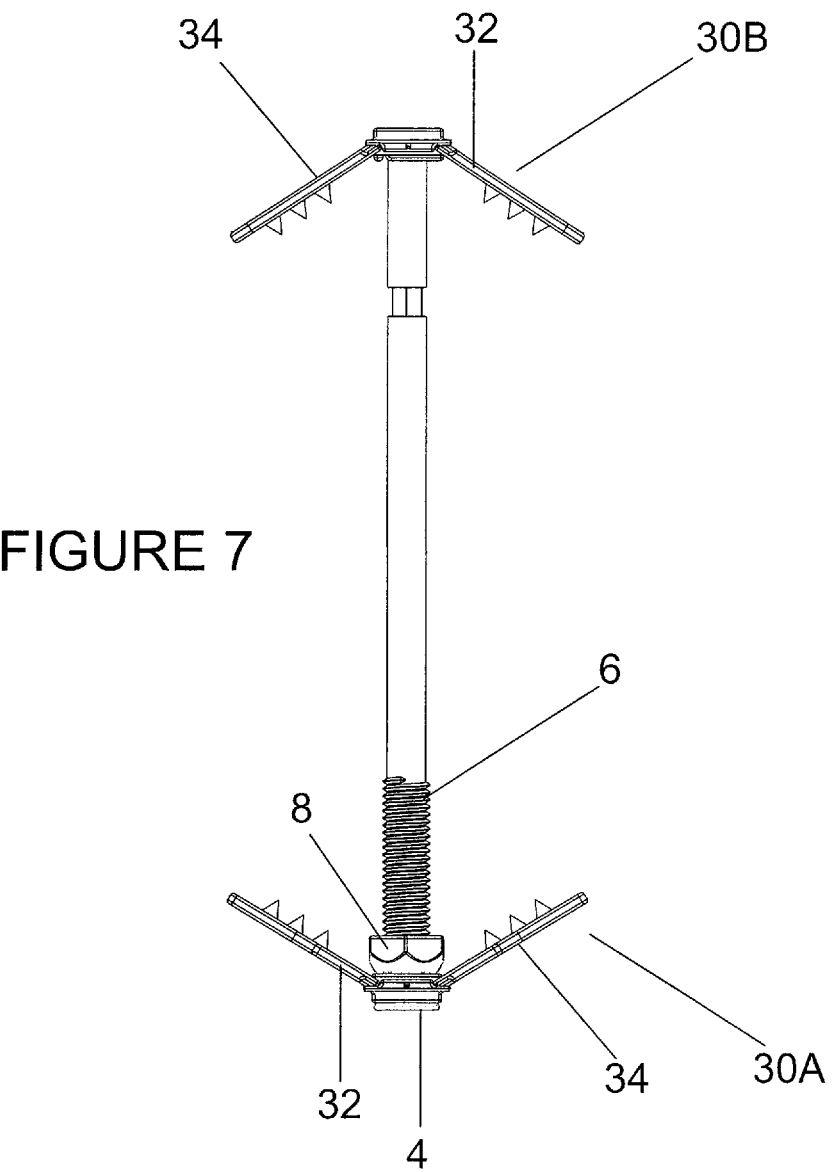
FIG. 7 is a schematic representation showing the wings of the spinous process fixation plates in the folded position prior to installation with respect to the spinous process bone.

FIG. 7 is a schematic representation showing the wings 32 and 34 of the spinous process fixation plates 30A and 30 B in the folded position prior to final installation with respect to the spinous process bone.

The spinous fixation device is devised as a minimally invasive laterally placed percutaneous fusion device. The method for inserting the intraspinous device is as follows. Following the lateral fusion of the adjacent vertebrae, a long, thin, blunt dilator can be passed from the posterior aspect of the lateral incision (or in cases where tow incisions are used, we would use the posterior incision which is lateral to the paraspinal muscles), gently through the paraspinal muscles, to the interspinous segment at the level of interest. The surgeon's other finger is placed in the retroperitoneal space during placement of the first dilator, and used to make sure that the dilator does not pass through the quadratus lumborum and into the retroperitoneal space, but rather is guided appropriately to the interspinous space. AP and lateral fluoroscopy images would be used to guide the correct placement of the first dilator. Thereafter, a second and then third larger dilator would be placed over the proceeding smaller dilators, and then a final retractor can be place over the largest dilator and fixed to the operating table. Light sources can then be dropped down to improve visualization. Blunt dissection, pituitary rongeurs, and or cautery can then be used to remove any soft tissue and expose the spinous process, on the ipsilateral side. The interspinous ligament can then be removed in the same manner. Great care is taken to respect and preserve the supraspinous ligament, which is important for overall stability. Once the interspinous ligament has been removed, various angled curettes were then used to perform a subperiosteal dissection of the spinous processes on the contralateral side. This is to provide good bony surface area for fixation for the contralateral plate, as well as to decorticate the surface somewhat for arthrodesis. Once the contralateral subperiosteal dissection had been completed, the distal or contralateral plate 30A that is attached to the partially threaded bolt 2 is gently passed in a folded position, through the interspinous, and into the contralateral paraspinal muscles. By tightening down on the deployment nut 8, the wings 32 and 34 of the contralateral plate 30A are deployed or opened, and brought flush against the contralateral spinous process. Teeth 36 on the wings 32 and 34 are then sunk into the spinous process bone. A curette or drill can then be used to decorticate the bone in the interspinous region for the arthrodesis. The ipsilateral plate 30B is then deployed down the partially threaded bolt 2 in a folded fashion but in reverse orientation to that of contralateral plate 30A. Thereafter lag nut 10 to secure the ipsilateral plate 30B against the spinous process. A groove is provided in the partially threaded shaft 2 to insure that the ipsilateral plate 30B exactly matches the contralateral plate 30A in terms of position. A lock nut 12 is threaded downward on to lag nut 10 and tightened to hold the assembly firmly in place. Threaded apertures 38 in plates 30A and 30B are provided to place locking fasteners, such as bolts, into the spinous process to provide additional fixation if needed. Likewise the locking bolts may connect the contralateral plate to the ipsilateral plate where matching threads on each of the plates will accept the locking screws. The threaded bolt 2 is then cut above the lock nut 12 and removed. Alternatively the partially thread bolt 2 may be a two piece member that is threaded together at a location above the threaded portion 6. Upon completion of the procedure the portion above the threaded section 6 would be unscrewed from the thread section and removed from the patient. Bone graft material of choice can then be placed between the plates. AP and lateral fluoroscopy is used during the placement of the plate as needed to ensure the correct size and positioning of the plate.

In addition, if the patient is already in the prone position, the plates 30A and 30B can be placed in a similar fashion through a unilateral or bilateral posterior lateral incision. The intraspinous process fixation device itself can also be dynamized, to allow for either less stress shielding of the anterior interbody spacer (so called soft stabilization), or it could be used as an interspinous process distraction device, to prevent hyperextension and buckling of the ligamentum flavum in cases of spinal stenosis.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinous process fixation device comprising:
   a partially threaded bolt;
   a first fixation plate having a first wing portion and a second wing portion, said first wing portion having a pair of side walls extending away from one end, said second wing portion having a pair of side walls extending away from one end;
   a second fixation plate having a third wing portion and a fourth wing portion, said third wing portion having a pair of side walls extending away from one end, said fourth wing portion having a pair of side walls extending away from one end, said second fixation plate independently movable along a longitudinal axis of said bolt relative to said first fixation plate and said first fixation plate independently movable along said longitudinal axis of said bolt relative to said second fixation plate;
   said pair of side walls of said first wing portion and said pair of side walls of said second wing portion are configured to receive a pivot element when brought in alignment whereby said first wing portion is pivotally connected to said second wing portion by said pivoting element, said first fixation plate is traversable between a first position and a second position, said first fixation plate being independently traversable relative to said second fixation plate;
   said pair of side walls of said third wing portion and said pair of side walls of said forth wing portion are configured to receive a pivot element when brought in alignment whereby said third wing portion is pivotally connected to said fourth wing portion by said pivoting element whereby said second fixation plate is traversable between a first position and a second position, said second fixation plate being independently traversable relative to said first fixation plate;
   said first fixation and said second fixation plate being mounted on said partially threaded bolt;
   said first fixation plate being adapted to operatively engage a first surface of a spinous process bone and said second fixation plate being adapted to operatively engage a second surface on the spinous process bone which is located on the spinous process bone on a side opposite said first surface of said spinous process bone.

2. The spinous process fixation device of claim 1 wherein said partially threaded bolt has a lag nut threaded on to the threaded section of said partially threaded bolt, said lag nut including a surface that is in operative engagement with at least one beveled surface formed on said second fixation plate.

3. The spinous process fixation device of claim 2 wherein said lag nut is located on one side of said second fixation plate and a deployment nut is located on an opposite side of said second fixation plate.

4. The spinous process fixation device of claim 3 wherein said partially threaded bolt has a locking nut threaded on to the threaded section of said partially threaded bolt, said locking nut including a surface in operative engagement with said lag nut, whereby said threaded bolt, said first and second fixation plates, and said deployment and lag nut are maintained in a fixed relationship.

5. The spinous process fixation device of claim 1 wherein said partially threaded bolt has a deployment nut threaded on to the threaded section of said partially threaded bolt, said deployment nut including a surface that is in operative engagement with at least one beveled surface formed on said first fixation plate.

6. The spinous process fixation device of claim 5 wherein an enlarged bolt head is located on one side of said first fixation plate and said deployment nut is located on an opposite side of said first fixation plate.

7. The spinous process fixation device of claim 1 wherein said partially threaded bolt includes an enlarged bolt head, said enlarged bolt head including a surface that is in operative engagement with at least one beveled surface formed on said first fixation plate.

8. The spinous process fixation device of claim 1 wherein the first wing portion, the second wing portion, the third wing portion and the fourth wing portion each include a offset portion, whereby multiple levels of fixation of adjacent spinous process bone can be performed without fixation plate overlap.

9. The spinous process fixation device of claim 1 wherein the first wing portion, the second wing portion, the third wing portion and the fourth wing portion each include a plurality of teeth, whereby said first and section fixation plates can be anchored to said spinous process bone.

10. The spinous process fixation device of claim 1 wherein the first wing portion, the second wing portion, the third wing portion and the fourth wing portion each include a plurality of threaded apertures, said apertures on said first and second fixation plates being in alignment with one another whereby said first and second fixation plates can be connected to one another one another by a fastener that is threaded through said first and second fixation plates to permit additional anchoring of the first and second fixation plates to the spinous process bone and to one another.

* * * * *